US011168454B2

(12) United States Patent
Nichols

(10) Patent No.: US 11,168,454 B2
(45) Date of Patent: Nov. 9, 2021

(54) DYNAMIC AUTONOMOUS SOIL MOISTURE CONTROL

(71) Applicant: Trimble Inc., Sunnyvale, CA (US)

(72) Inventor: Mark Nichols, Christchurch (NZ)

(73) Assignee: Trimble Inc., Sunnyvale, CA (US)

( * ) Notice: Subject to any disclaimer, the term of this patent is extended or adjusted under 35 U.S.C. 154(b) by 173 days.

(21) Appl. No.: 16/380,284

(22) Filed: Apr. 10, 2019

(65) Prior Publication Data

US 2020/0325647 A1      Oct. 15, 2020

(51) Int. Cl.
| | | |
|---|---|---|
| *E02D 1/00* | (2006.01) | |
| *A01G 25/16* | (2006.01) | |
| *E02D 3/12* | (2006.01) | |
| *B05C 5/02* | (2006.01) | |
| *E02D 1/02* | (2006.01) | |
| *G01N 33/24* | (2006.01) | |

(52) U.S. Cl.
CPC .......... *E02D 3/123* (2013.01); *A01G 25/167* (2013.01); *B05C 5/0225* (2013.01); *E02D 1/027* (2013.01); *G01N 33/246* (2013.01); *E02D 2600/10* (2013.01)

(58) Field of Classification Search
CPC ...... A01G 25/167; G01N 33/246; E02D 3/10; E02D 3/12; E02D 3/123; E02D 1/027; E02D 2600/10; E02D 3/026; A01B 29/045; E01C 19/23
USPC ...................... 405/37; 137/78.2, 78.3; 239/63
See application file for complete search history.

(56) References Cited

U.S. PATENT DOCUMENTS

| | | | | |
|---|---|---|---|---|
| 5,220,876 A | * | 6/1993 | Monson ............... | A01B 79/005 111/130 |
| 6,510,367 B1 | * | 1/2003 | McQuinn ............. | A01B 79/005 700/241 |
| 7,502,665 B2 | * | 3/2009 | Giles .................... | A01B 79/005 700/241 |
| 2004/0193348 A1 | | 9/2004 | Gray et al. | |
| 2007/0239338 A1 | * | 10/2007 | Potts .................... | E01C 19/288 701/50 |

(Continued)

OTHER PUBLICATIONS

Extended European Search Report for Application No. 20167741. 6-1002, dated Sep. 9, 2020, 7 pages.

(Continued)

*Primary Examiner* — Sunil Singh
(74) *Attorney, Agent, or Firm* — Kilpatrick Townsend & Stockton

(57) ABSTRACT

Embodiments describe a method for moisturizing soil at an open construction site. The method includes determining a target soil moisture level for the soil at the open construction site; measuring a current soil moisture level of a location within the open construction site with a moisture sensor while the moisture control system is moving along a predetermined path across the site; storing the current soil moisture level of the location in memory; determining a target volume of water for achieving the target soil moisture level at the location based on the current soil moisture level at the location; calculating a target application rate to achieve the target soil moisture level at the location based on the target volume of water; and applying the target volume of water at the target application rate to the location when the system is positioned to dispense water at the location of the site.

20 Claims, 8 Drawing Sheets

(56) References Cited

U.S. PATENT DOCUMENTS

| | | |
|---|---|---|
| 2008/0202777 A1 | 8/2008 | Corcoran |
| 2012/0130552 A1* | 5/2012 | Schmidt .................. A01G 25/09 700/284 |
| 2016/0255763 A1* | 9/2016 | Canyon ................. A01B 79/005 |
| 2016/0298306 A1 | 10/2016 | De Kontz et al. |
| 2018/0024563 A1 | 1/2018 | Matsuzaki et al. |
| 2020/0196515 A1 | 6/2020 | Engel |
| 2020/0326716 A1* | 10/2020 | Nichols ............... B05C 11/1015 |

OTHER PUBLICATIONS

U.S. Appl. No. 16/380,282, "First Action Interview Pilot Program Pre-Interview Communication", filed Apr. 7, 2021, 8 pages.

* cited by examiner

DYNAMIC AUTONOMOUS SOIL MOISTURE CONTROL

BACKGROUND

Construction of a structure, e.g., a building, road, track, and the like, often requires the ground upon which it is built to be flat and firm so that adequate support can be provided for the structure. Before the structure can be constructed, vegetation and/or top soil located at the construction location is often removed to form an open construction site. Then, the exposed ground is moistened by a water truck and subsequently flattened and compacted by a roller truck that is repeatedly driven over the open construction site.

Rolling over the ground in the open construction area, however, can eject dust into the air which can be a nuisance to people around the construction site. Furthermore, the degree of compactness and uniformity across the open construction site achieved by the roller truck largely depends on the level of moisture of the soil and its uniformity across the open construction site. The level of success in achieving the desired level of flatness and firmness often hinges on the skill and experience level of the operator of a water truck that sprays the soil to achieve a suitable uniformity and degree of moisture. Existing water trucks, however, are limited in their ability to assist in achieving a uniform and correct level of moisture across an open construction site. As such, improvements are desired.

SUMMARY

Embodiments provide soil moisture control systems and methods for automating the dispensing of water to achieve a highly uniform and accurate level of moisture across an open construction site. The soil moisture control system can be an electronic system installed on a water truck that includes a soil moisture control module specifically configured to receive and analyze information from a variety of information modules and calculate an application rate and volume of water to dispense onto the ground. The soil moisture control module can then guide the water truck across the open construction site, autonomously or by instructing a user, to achieve a highly uniform and accurate level of moisture across the open construction site, which can significantly improve the flatness and compactness of the ground achieved following soil compaction and/or control the amount of dust that is ejected into the air.

In some embodiments, a method for moisturizing soil at an open construction site includes determining, by a soil moisture control system, a target soil moisture level for the soil at the open construction site; measuring, by the soil moisture control system, a current soil moisture level of a location within the open construction site with a moisture sensor while the moisture control system is moving along a predetermined path across the open construction site; storing, by the moisture control system, the current soil moisture level of the location in memory; determining, by the soil moisture control system, a target volume of water for achieving the target soil moisture level at the location based on the current soil moisture level at the location; calculating, by the soil moisture control system, a target application rate to achieve the target soil moisture level at the location based on the target volume of water; and applying, by the soil moisture control system, the target volume of water at the target application rate to the location when the system is positioned to dispense water at the location of the open construction site.

The location can be a first location and the method further comprises measuring, by the moisture control system, a current moisture level of a second location within the open construction site with the moisture sensor while the moisture control system is moving along the predetermined path across the open construction site. The second location can be located at a point farther along the predetermined path than the first location. The measuring of the current moisture level of the second location can occur while the water dispenser is dispensing water at the first location. The target soil moisture level can be based on binding characteristics of the soil to minimize dust or to achieve a certain level of soil compaction. Determining the target volume of water can be based on a difference between the target soil moisture level and the current soil moisture level. Determining the target volume of water can be based on forecast evaporation rates of the open construction site and a time at which a construction activity is to be performed at the open construction site following dispensing of water at the open construction site. The location can be a line of soil measureable by the moisture sensor. The system can include a water dispenser configured to dispense different volumes of water at different locations along the line of soil. The water dispenser can include a plurality of independently controllable nozzles.

In some embodiments, a computer product can include a non-transitory computer readable medium storing a plurality of instructions that when executed control an electronic device including one or more processors, the instructions including determining, by a soil moisture control system, a target soil moisture level for the soil at the open construction site; measuring, by the soil moisture control system, a current soil moisture level of a location within the open construction site with a moisture sensor while the moisture control system is moving along a predetermined path across the open construction site; storing, by the moisture control system, the current soil moisture level of the location in memory; determining, by the soil moisture control system, a target volume of water for achieving the target soil moisture level at the location based on the current soil moisture level at the location; calculating, by the soil moisture control system, a target application rate to achieve the target soil moisture level at the location based on the target volume of water; and applying, by the soil moisture control system, the target volume of water at the target application rate to the location when the system is positioned to dispense water at the location of the open construction site.

The location can be a first location and the method further comprises measuring, by the moisture control system, a current moisture level of a second location within the open construction site with the moisture sensor while the moisture control system is moving along the predetermined path across the open construction site. The second location can be located at a point farther along the predetermined path than the first location. The measuring of the current moisture level of the second location can occur while the water dispenser is dispensing water at the first location. The target soil moisture level can be based on binding characteristics of the soil to minimize dust or to achieve a certain level of soil compaction.

In some embodiments, a system for moisturizing soil at an open construction site includes one or more information modules configured to receive and send information, the one or more information modules including a moisture sensor positioned at a front of a water truck; memory configured to store data; a water dispenser positioned at a back of the water truck and configured to dispense water through one or more nozzles into the soil at the open construction site; a control interface for displaying information to a user; and a soil moisture control module formed of one or more processors coupled to the one or more information modules, the memory, the water dispenser, and the control interface. The soil moisture control module can be configured to determine a target soil moisture level for the soil at the open construction site; measure a current soil moisture level of a location within the open construction site with the moisture sensor while the moisture control system is moving along a predetermined path across the open construction site; store the current soil moisture level of the location in memory; determine a target volume of water for achieving the target soil moisture level at the location based on the current soil moisture level at the location; calculate a target application rate to achieve the target soil moisture level at the location based on the target volume of water; and apply the target volume of water at the target application rate to the location when the system is positioned to dispense water at the location of the open construction site.

The information modules can include at least one of a communication module, a positioning module, and an input device. The soil moisture control module can be coupled to a vehicle control system that includes a vehicle control module for controlling the operation of the water truck without user involvement. The vehicle control system can further include a camera, a distance sensor, and a motor with steering to control the operation of the water truck. The current site characteristics can include at least one of a temperature at the open construction site, wind speed and direction at the open construction site, and a slope gradient of one or more areas of the open construction site.

A better understanding of the nature and advantages of embodiments of the present invention may be gained with reference to the following detailed description and the accompanying drawings.

DETAILED DESCRIPTION

Embodiments describe a soil moisture control system for uniformly and accurately dispensing water across an open construction site. The soil moisture control system can include a control module that can receive data related to the characteristics of the open construction site from a variety of information modules. The control module can then use this data to guide the system across the open construction site while dispensing the correct volume of water at the correct application rate to achieve a uniform and accurate level of moisture across the open construction site.

In some instances, the soil moisture control system can include a water dispenser for dispensing the water from a water tank; and, the system can also include a control interface for displaying and/or receiving information to/from a user. The control interface can display instructions from the soil moisture control module to the user to instruct the user to guide the system along a predetermined path across the open construction site.

Furthermore, the soil moisture control system can be autonomous in some embodiments so that the movement across the open construction site and the rate and volume at which water is dispensed is solely controlled by the soil moisture control system with little to no user involvement. In such instances, the soil moisture control module can be further configured to send controls to a vehicle control module to directly control the movement of the water truck.

As will be discussed further herein, the soil moisture control system is an improvement upon conventional water trucks, which are basic trucks fitted with a water tank that solely rely on a user to guide and dispense water across the open construction site. The volume and rate of water dispensed by the water truck, and the uniformity of moisture across an area of the open construction site, is therefore solely dependent on the user's skills. Accordingly, the level of moisture achieved by a conventional water truck across an open construction site may be non-uniform and have improper levels of moisture, which can substantially affect soil compaction and dust control for reasons discussed herein.

I. Soil Compaction and Dust Control for an Open Construction Site

Figure 1A:
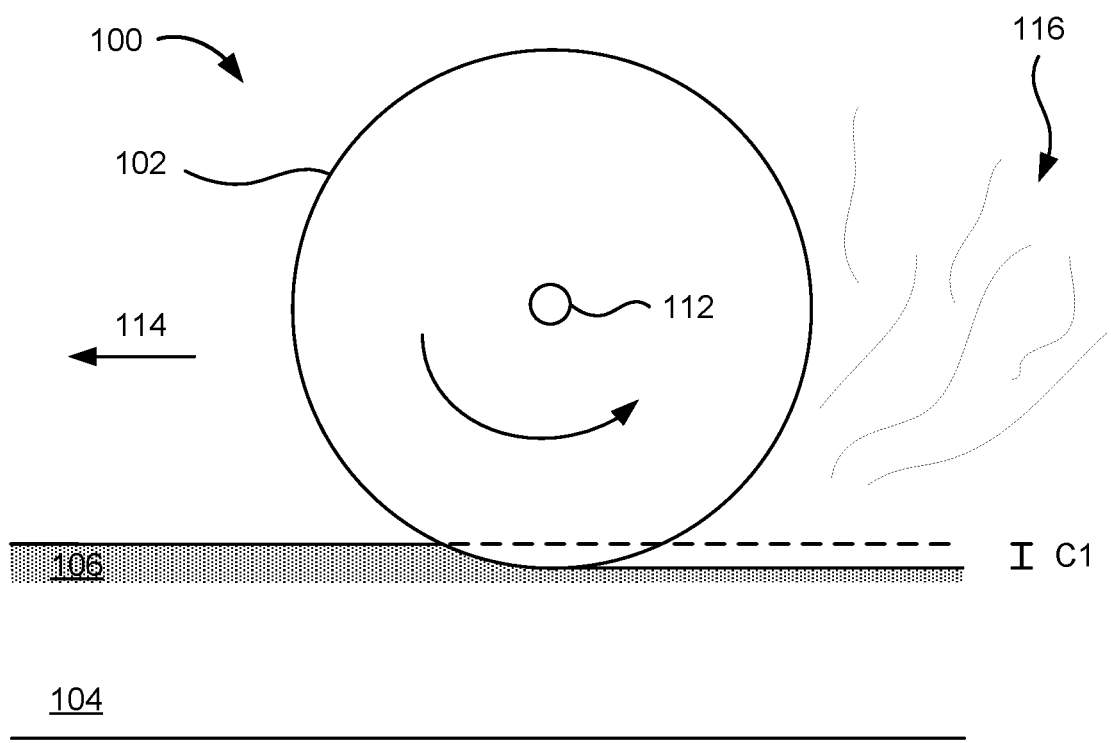
FIG. 1A is a basic illustration of a drum of a roller truck passing over a ground region of an open construction site having little to no moisture.
Figure 1B:
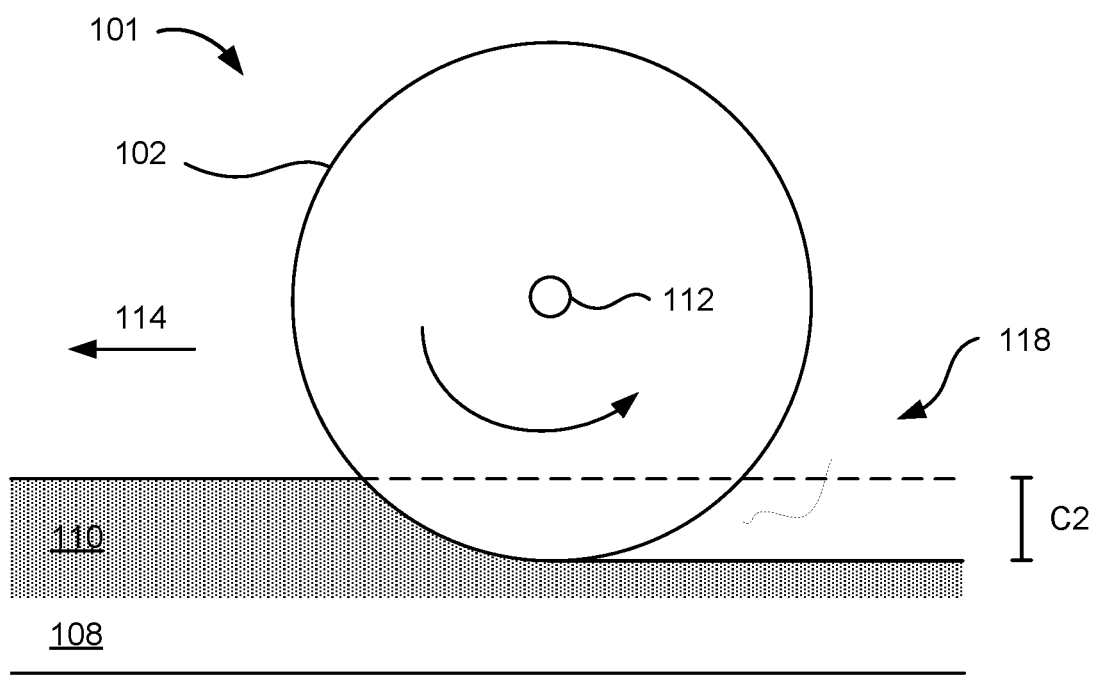
FIG. 1B is a basic illustration of drum passing over a ground region of an open construction site having an adequate level of moisture.

FIGS. 1A and 1B illustrate how moisture can affect soil compaction and dust generation by a roller truck driving on an open construction site. Specifically, FIG. 1A is a basic illustration 100 of a drum 102 of a roller truck passing over a ground region 104 of an open construction site having little to no moisture 106, while FIG. 1B is a basic illustration 101 of drum 102 passing over a ground region 108 of an open construction site having an adequate level of moisture 110.

As shown in FIG. 1A, drum 102 may rotate around an axle 112 as the roller truck moves along direction 114 across open construction site 104. Because ground region 104 has little to no moisture 106, the binding characteristics of the dry soil may be unsuitable for compaction and only result in a small degree of compaction C1. Having a small degree of compaction C1 with each pass of the roller truck can require a higher number of passes to achieve a target degree of soil compaction, which can result in higher cost and longer construction times. Furthermore, the low moisture in the soil may result in the generation of dust 116 that may be ejected into the air as drum 102 agitates the dry soil. Dust 116 can float in the air to neighboring regions and become a nuisance to those around the construction site.

With the right amount of moisture, however, a greater degree of compaction and little to no generation of dust can be achieved. For instance, ground region 108 of the open construction site in FIG. 1B can have an adequate amount of moisture 110 in its soil. Thus, the binding characteristics of the moist soil may be suitable for compaction and result in a greater degree of compaction C2 when compared to dry soil. Having a larger degree of compaction C2 with each pass of the roller truck can decrease the number of passes for achieving a target degree of soil compaction, which can result in lower cost and shorter construction times. Furthermore, the adequate moisture in the soil may decrease, or completely prevent, the generation of dust 118 that is ejected into the air as drum 102 agitates the moist soil. For soil compaction, it may be possible for the soil to have too much moisture. When there is too much moisture in the soil, the soil may be overly compacted and too dense. Thus, the soil needs to be at the right moisture level to enable acceptable soil compaction.

In addition to dispensing the right level of moisture at the open construction site, the moisture may also need to be evenly and uniformly applied across the entire open construction site. Conventionally, a user drives a water truck across the open construction site, visually observes which areas need more water, and then drives the water truck in that direction while dispensing a certain amount of water determined by the user, all based on the individual experience and skill level of the user.

Figure 2:
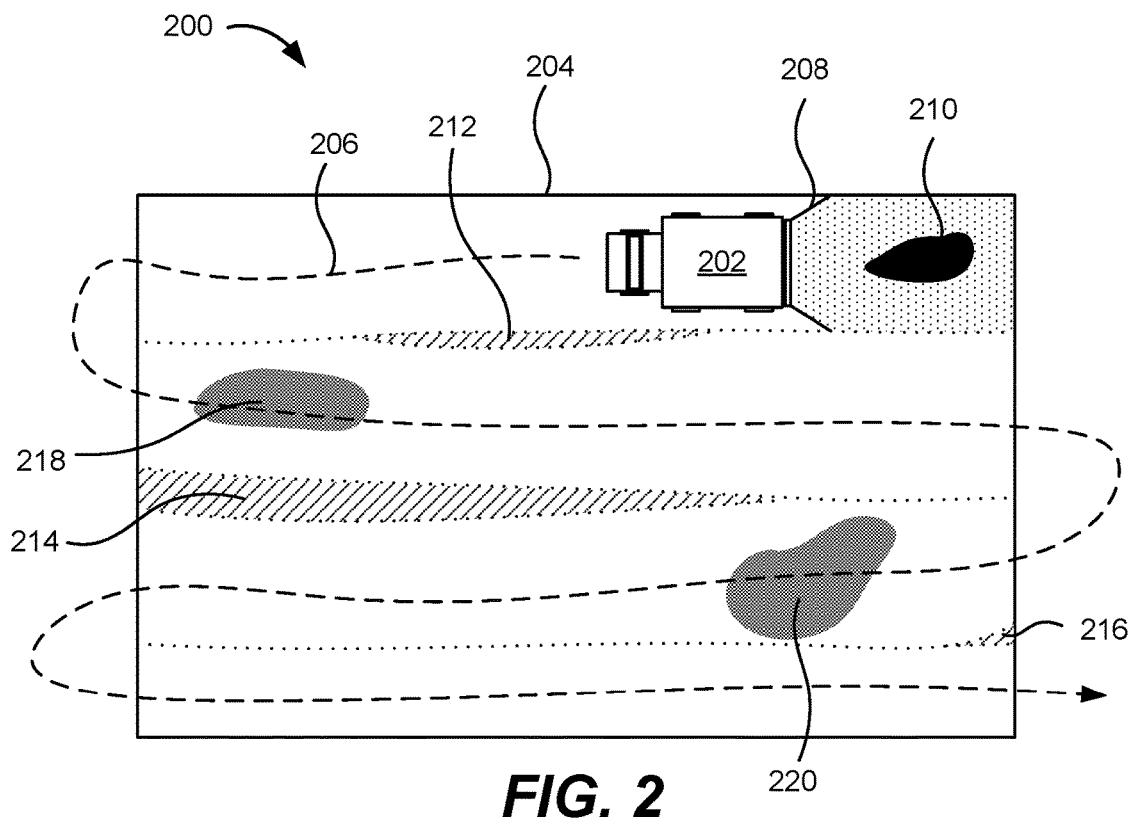
FIG. 2 is a simplified top-down illustration of a water truck that is dispensing water on an open construction site without a soil moisture control system.

For instance, FIG. 2 is a simplified top-down illustration 200 of a user driving a water truck 202 and dispensing water on an open construction site 204. Vegetation and top soil can be removed at the open construction site to reveal underlying soil that is compactable and suitable for being used as foundation for a structure. To moisten the exposed soil for soil compaction and/or dust control, the driver may steer water truck 202 along path 206 across site 204 while water 208 is being dispensed from water truck 202. The driver can traverse path 206 based on his or her perceived location, visual inspection of the ground moisture, and personal skill and experience. Even though the driver may believe that he or she is evenly and uniformly applying moisture across open construction site 204, in reality, he or she may be causing some areas 210 to have moisture levels that are too high while leaving other areas 212, 214, and 216 with moisture levels that are too low. Areas that already contain moisture, e.g., areas 218 and 220 that exist due to collected moisture, such as from rain water, may end up having moisture levels that are too high once water truck 202 dispenses more water as it passes over them. Areas with moisture levels that are too low can be created by gaps in water dispensing coverage from user error. The non-uniform moisture and unsuitable levels of moisture can cause issues when open construction site 204 is compacted by a roller truck.

II. Autonomous Soil Moisture Control

According to some embodiments of the present disclosure, a soil moisture control system can be configured to autonomously determine the correct volume and application rate, as well as an ideal path, for dispensing water on an open construction site. The control system can use this information to guide the water truck along the ideal path across the site while dispensing the correct volume of water at the correct application rate to maximize uniformity and coverage of a target level of moisture across the open construction site.

Figure 3:
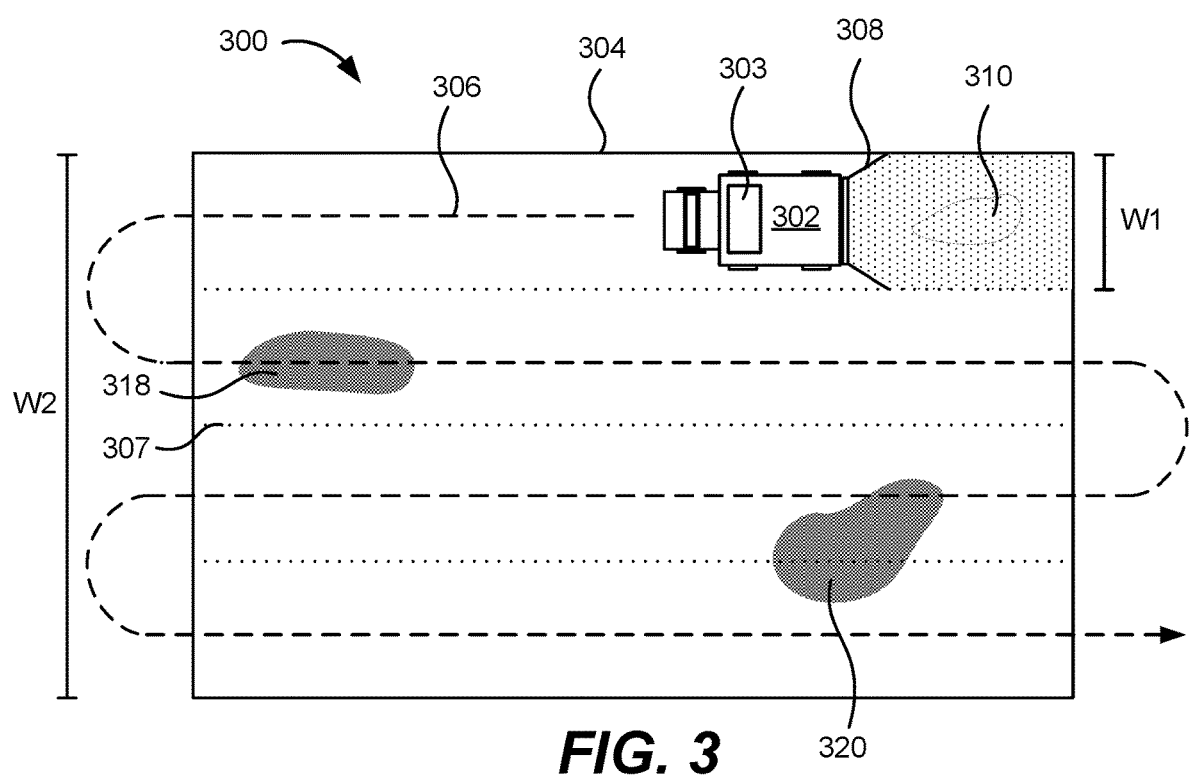
FIG. 3 is a simplified top-down illustration of a water truck configured with a soil moisture control system that is dispensing water on an open construction site, according to some embodiments of the present disclosure.

FIG. 3 is a simplified top-down illustration 300 of a water truck 302 configured with a soil moisture control system 303 that is dispensing water on an open construction site 304, according to some embodiments of the present disclosure. Soil moisture control system 303 can be an electronic device, or more than one electronic device, that is implemented on water truck 302 to improve the operation of water truck 302, according to some embodiments of the present disclosure. In open construction site 304, vegetation and top soil can be removed to reveal underlying soil that is compactable and suitable for being used as foundation for a structure. To moisten the exposed soil for soil compaction and/or dust control, water truck 302 may be steered along a predetermined path 306 across open construction site 304 while water 308 is dispensed by water truck 302. In some embodiments, soil moisture control system 303 can include a control interface that can provide graphical instructions to a user, i.e., driver of water truck 302, to guide water truck 302 along path 306. By providing a graphical interface to the user, an inexperienced user may achieve results commensurate with an experienced user as the discrepancy in skill level can be minimized by the assistance of soil moisture control system 303. As will be further appreciated herein with respect to FIG. 4, soil moisture control system 303 can be configured to communicate with a vehicle control module of water truck 302 so that soil moisture control system 303 can autonomously drive water truck 302 to guide it along path 306 without user involvement.

In some embodiments, predetermined path 306 can be calculated by soil moisture control system 303 based on the dimensions of open construction site 304 and a width W1 of water coverage dispensed by water truck 302. Path 306 can be determined so that edges 307 of water coverage efficiently overlap one another to mitigate or completely eliminate gaps of overlaps in water coverage to ensure that the entire surface area of open construction site 304 receives the correct amount of moisture. For instance, if open construction site 304 has a total width of W2, then path 306 can be configured to make W2/W1 number of passes across open construction site 304. If W2/W1 does not divide into whole integers, i.e., results in three and a half passes, then soil moisture control system 303 can, during the final pass, dispense water by using only those nozzles of water truck 302 that do not overlap with areas already dispensed with water from the previous pass to avoid oversaturating the soil in overlapping regions. A complete path 306 can be referred to as a pass that is repeated over open construction site 304 a certain number of times to achieve a target moisture level, as will be discussed further herein. Furthermore, soil moisture control system 303 can identify areas that already have elevated levels of moisture, e.g., areas 310, 318, and 320, system 303 can be configured to cease the dispensing of water on those areas to avoid oversaturation. Such embodiments where control system 303 can control the operation of individual nozzles are discussed further herein with respect to FIG. 9B. Accordingly, water trucks configured with soil moisture control systems discussed herein can achieve a uniform and accurate level of moisture across the open construction site, as shown in FIG. 3. The uniform and suitable levels of soil moisture across open construction site 304 can result in an even and sufficiently compact foundation once open construction site 204 is compacted by a roller truck.

III. Method of Autonomous Moisture Control

Figure 4:
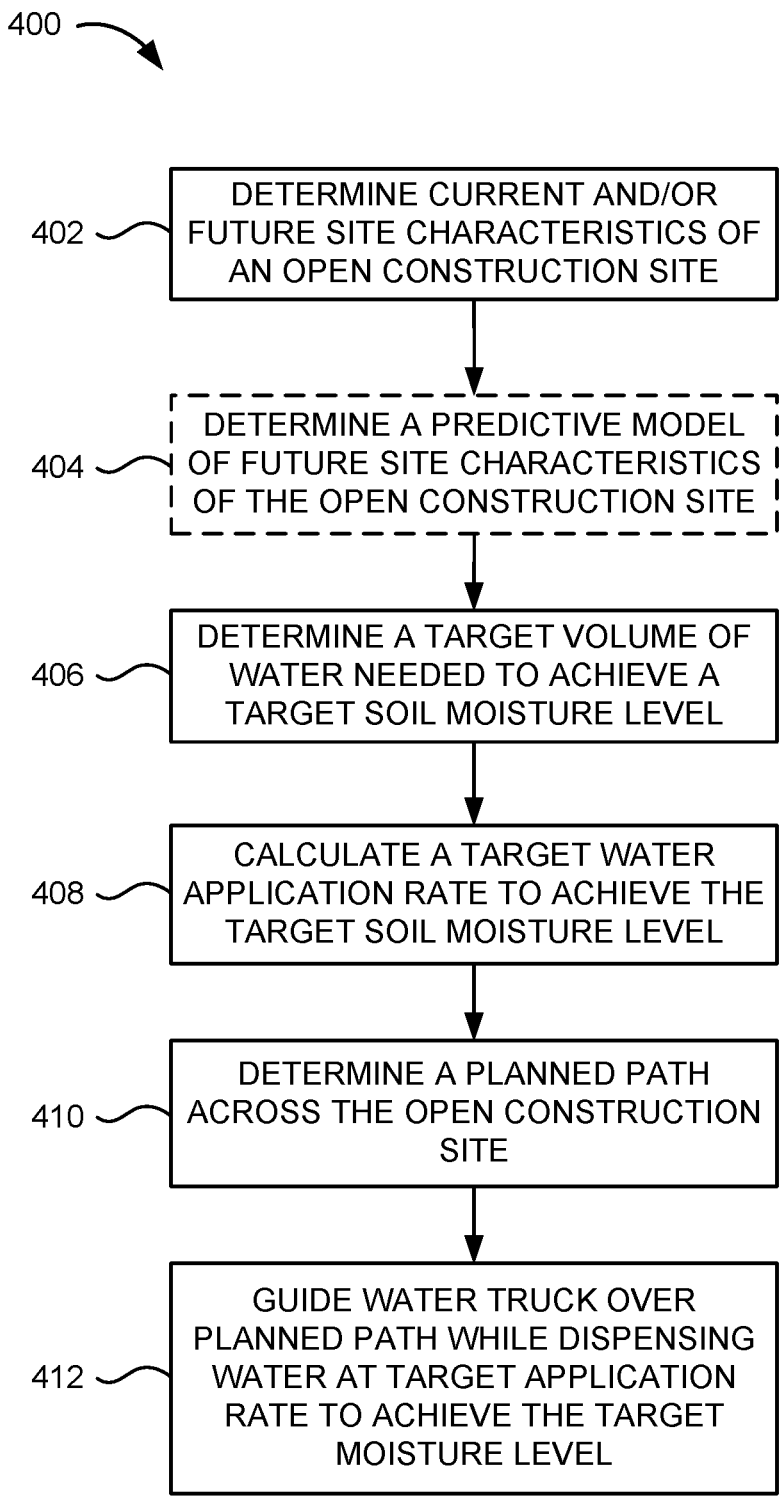
FIG. 4 is a flow chart of an exemplary method performed by a soil moisture control system for achieving uniform and suitable levels of moisture across an open construction site, according to some embodiments of the present disclosure.
Figure 5:
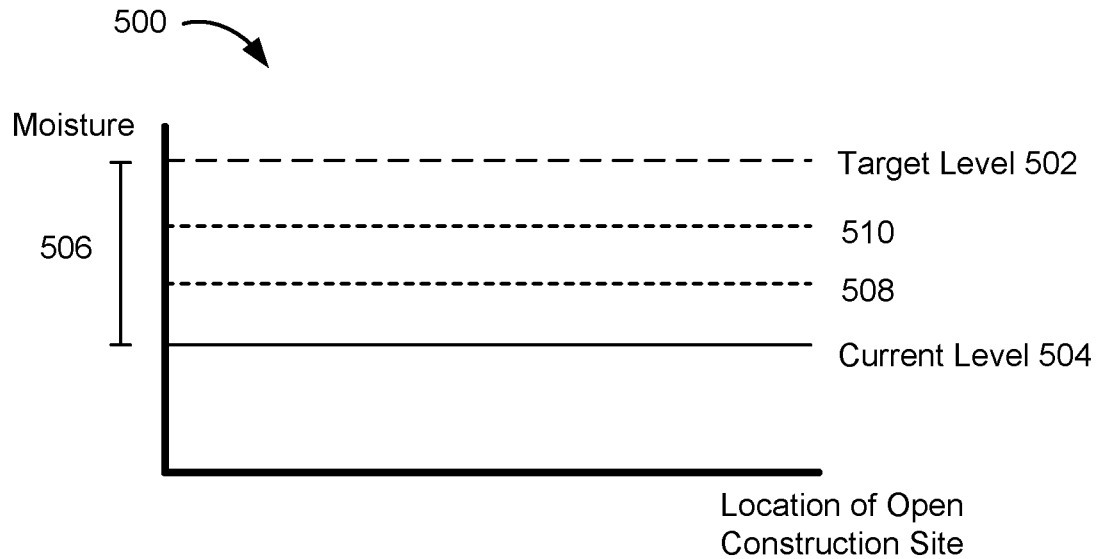
FIG. 5 is a graph illustrating an exemplary target moisture level and an exemplary current moisture level, according to some embodiments of the present disclosure.
Figure 6:
FIG. 6 is a graph illustrating an exemplary target volume of water based on difference between current and target moisture levels, according to some embodiments of the present disclosure.

FIG. 4 is a flow chart 400 of an exemplary method performed by a soil moisture control system for achieving uniform and suitable levels of moisture across an open construction site, according to some embodiments of the present disclosure. FIGS. 5-6 are referenced during the discussion of FIG. 4 to help illustrate the concepts discussed in FIG. 4. FIGS. 5-6 are graphs illustrating how an exemplary volume of water for achieving a target moisture level is calculated in some embodiments.

At block 402, current and/or future site characteristics of an open construction site can be determined. Current site characteristics can be any data representative of a current environmental or physical condition at the open construction site. As an example, the system can analyze a slope gradient and direction of the surface topography of the open construction site to identify how water may flow when dispensed on the soil. The slope gradient and direction of the surface topography can be measured by any suitable device at the construction site. The system can also analyze the current temperature at the open construction site with a local thermometer to determine the degree of evaporation of moisture at the construction site.

Temperatures above a threshold value, i.e., approximately 80° F., can result in a high rate of evaporation, and thus the soil moisture control system may increase the volume of water to dispense at the location, or vice versa when the temperature is lower than 80° F. Some other current site characteristics include wind speed and direction, where higher wind speeds may result in higher rates of evaporation and thus result in a larger volume of water to dispense at the construction site, and amount of rainfall measured by digital rain gauges around the open construction site, i.e., Rain-Wave® information from Trimble, Inc.

Future characteristics of the open construction site can be any data representative of environmental or physical conditions at the open construction site that may occur in the future. For determining the future characteristics of the site, the system can receive predictive forecast information from various public information modules, such as local weather forecast databases and Doppler radar data for identifying predictive weather models for various weather factors such as, but not limited to, rainfall, cloud cover, temperature, wind speed, and wind direction. The current and/or future site characteristics data can be stored in memory and accessed by a processor of the soil moisture control system for various purposes.

As an example, at block 404, the soil moisture control system can optionally use the future site characteristics to determine a predictive model of the open construction site. The predictive model can be a model that is designed to give an estimation of the environmental and/or physical conditions of the open construction site across one or more time periods in the future. For instance, the predictive model can estimate that the predicted temperature and wind speed that the open construction site will experience in 5 days will result in a large amount of moisture evaporation, and that the temperature and wind speed will then drop thereafter which will result in a small amount of moisture evaporation after the 5 days. Or, the predictive model can estimate that an amount of rainfall will be experienced by the open construction site within the next 5 days.

The predictive model and the forecast evaporation rates can be used by the soil moisture control system to more accurately calculate a target water application rate and target volume of water to dispense on the soil at the open construction site. In some embodiments, this is particularly beneficial when the date of soil compaction is known and scheduled for a certain time in the future. The predictive model can also allow the system to provide impact estimates should the soil compaction be delayed.

At block 406, a target volume of water needed to achieve a target soil moisture level can be determined. In some embodiments, the target volume of water can be determined based on a current soil moisture level and a target soil moisture level. The current soil moisture level can be determined by weighing and/or performing calculations on the current site characteristics of the open construction site. The target soil moisture level, on the other hand, can be a desired moisture level based on the desired goal to be achieved. For dust control, the target soil moisture level may be an amount of moisture that minimizes dust from being ejected into the atmosphere when construction activity is performed on the open construction site. In such instances, the target soil moisture level can be any level of moisture greater than a moisture level threshold without an upper moisture limit as there may not be a great concern for soil oversaturation for dust control. For soil compaction, the target soil moisture level may be an amount of moisture that achieves a target compaction level. In such instances, the target soil moisture level can be a range of levels of moisture between a minimum moisture level and a maximum moisture level. The target soil moisture level can also depend on soil type. Different soil types have different binding characteristics and thus require different moisture levels to enable sufficient soil compaction. A single open construction site can include many different soil types. Thus, an open construction site can have different target soil moisture levels for different areas of the open construction site. In some embodiments, the current soil moisture level and target soil moisture level can be determined by an engineer or scientist surveying the soil moisture at the open construction site. In such instances, the target soil moisture level can simply be acquired by the soil moisture control system as an input via a user interface.

In some embodiments, the target volume of water can be based on a difference between the current soil moisture level and the target soil moisture level of the open construction site. FIG. 5 is a graph 500 illustrating an exemplary target moisture level 502 and an exemplary current moisture level 504, according to some embodiments of the present disclosure. Graph 500 can have a y-axis representing moisture levels increasing upwards and an x-axis representing locations across an open construction site. For ease of understanding, the graph only illustrates horizontal locations across an area within the open construction site, even though the area construction site may have a two-dimensional (i.e., horizontal and vertical) configuration. And, the graph assumes that the current moisture level is constant across the entire open construction site. As shown in FIG. 5, current moisture level 504 can be subtracted from target moisture level 502 and result in a difference 506. Then, a target volume of water can be calculated based on difference 506 in the moisture levels, as shown in FIG. 6.

FIG. 6 is a graph 600 illustrating an exemplary target volume of water 602 based on difference 506 between current and target moisture levels, according to some embodiments of the present disclosure. Graph 600 can have an x-axis representing moisture levels increasing upwards and an x-axis representing horizontal locations across an open construction site for ease of discussion. Target volume of water 602 can be a volume of water that achieves the target soil moisture level when dispensed into the soil at the open construction site. In some embodiments, once the target volume of water is determined, it can be adjusted higher or lower based on various factors, such as a time delay and the future characteristics/predictive model of the open construction site. The time delay can be a time at which a construction activity (e.g., soil compaction or a construction activity that will generate dust) that will be performed at the construction site. As an example, target volume of water 602 may be adjusted to be higher 603 when a construction activity is planned to be performed at a later time, e.g., days or even weeks later, and a high rate of evaporation due to high temperatures and/or wind speed is predicted to occur during that time. As another example, target volume of water 602 may be adjusted to be lower 605 when a construction activity is planned to be performed at the later time and rainfall is predicted to occur during that time. In some embodiments, target volume of water 602 may not need to be adjusted if the construction activity is planned to be performed immediately after the soil is moistened. Accordingly, the system can preemptively compensate for expected moisture changes due to evaporation and/or rainfall during the time leading up to the construction activity.

With reference back to FIG. 4, the soil moisture control system can then, at block 408, use the determined target volume of water to calculate a target water application rate to dispense on the soil at the open construction site to achieve the target soil moisture level. The target application rate can be based on several factors, such as flow rate limits of the nozzles that dispense the water, capacity of the tank storing the water, the speed at which the truck is moving across the open construction site while it is dispensing water, and other factors.

Nozzle flow rate limits set an upper bound to the application rate. As such, knowing the nozzle flow rate limits can help the system select a suitable application rate that does not constantly operate the nozzle near its limits, which can maximize its usable lifespan and therefore improve the reliability of the soil moisture control system. Capacity of the tank can affect the length of operation before fill-ups. In some instances, it may be desirable to minimize refilling of the tank while the system is in the middle of traversing a path over the open construction site, and to maximize refilling of the tank when the system is finished traversing a path and is in between passes. Thus, the application rate of the water can be selected such that the entire contents of the tank are not dispensed until a pass is completed. The speed of the truck can affect the application rate because the faster the truck moves, the less water is dispensed at a specific location, and vice versa. If the flow rate of the nozzles is constant, the speed of the truck can be varied to achieve the target application rate.

In some embodiments, a single pass over the open construction site may not be possible for various reasons, e.g., nozzle flow rate limits, tank capacity, and/or truck speed settings. Thus, more than one pass may be necessary. In such instances, the target volume of water dispensed during each pass can be configured so that the target volume of water is achieved after the final pass is performed. As an example, with reference to FIG. 6, if target volume of water 602 is sought to be obtained but the nozzle flow rate, water storage capacity, and truck speed settings can only reasonably dispense a third of target volume of water 602, then the application rate can be calculated so that each pass dispenses an amount 604 per pass (i.e., a third of target volume of water 602). Thus, with each subsequent pass of the open construction site, referring briefly back to FIG. 5, the moisture level can increase from its current moisture level 504 to moisture level 508 after one pass, moisture level 510 after two passes, and target moisture level 502 after three passes. By being capable of calculating the application rate based on such factors, the soil moisture control system can improve the operation and ability of the water truck to accurately achieve a uniform and sufficient moisturizing of the soil at the open construction site in a timely manner.

With reference back, to FIG. 4, at block 410, a planned path across the open construction site to achieve a desired level of uniformity of moisture across the open construction site can be determined by the soil moisture control system. For instance, a predetermined path, e.g., path 306 discussed herein with respect to FIG. 3, can be calculated by soil moisture control system based on the dimensions of the open construction site and a width of water coverage dispensed by the water truck. The predetermined path can be determined so that edges of water coverage are positioned to mitigate or completely eliminate gaps or overlaps in water coverage to ensure that the entire surface area of the open construction site receives a correct amount of moisture.

At block 412, the soil moisture control system can then guide a water truck, in which the soil moisture control system is implemented, over the path while dispensing water at the target application rate to achieve the target soil moisture level. In some embodiments, the soil moisture control system can output a graphical interface to a user to guide the water truck along the path at a predetermined speed. The graphical interface can be displayed to the user on a display that indicates to the user where and at what speed to drive water truck along the open construction site. In additional or alternative embodiments, the soil moisture control system can autonomously instruct a vehicle control module to steer the water truck at the predetermined speed without user involvement. In such embodiments, the system can determine its location via positioning systems, e.g., global positioning systems (GPS), and determine its proximity to objects at the open construction site via distance sensors, e.g., light detection and ranging (LIDAR) sensors, and then instruct a vehicle control system to move and steer the water truck along the predetermined path at the correct speed on its own, as will be discussed further herein with respect to FIG. 11.

By being configured to perform method 400, soil moisture control systems, according to some embodiments of the present disclosure, can accurately and uniformly dispense an amount of moisture across an open construction site to achieve a target moisture level with little to no user involvement. Such systems can thus result in a water truck that is improved over conventional water trucks.

IV. Dynamic Autonomous Soil Moisture Control

According to some embodiments of the present disclosure, soil moisture control systems can be configured to measure a current moisture level of the soil at a location of the open construction site, calculate a volume of water to dispense at the location of the open construction site, and dispense the volume of water at the location of the open construction site at the correct application rate, all while the soil moisture control system is moving along the open construction site. This real-time measuring, calculating, and dispensing is referred herein as dynamic, or "on-the-fly", soil moisture control. An example of such as system is shown in FIGS. 7A-7B.

Figure 7A:
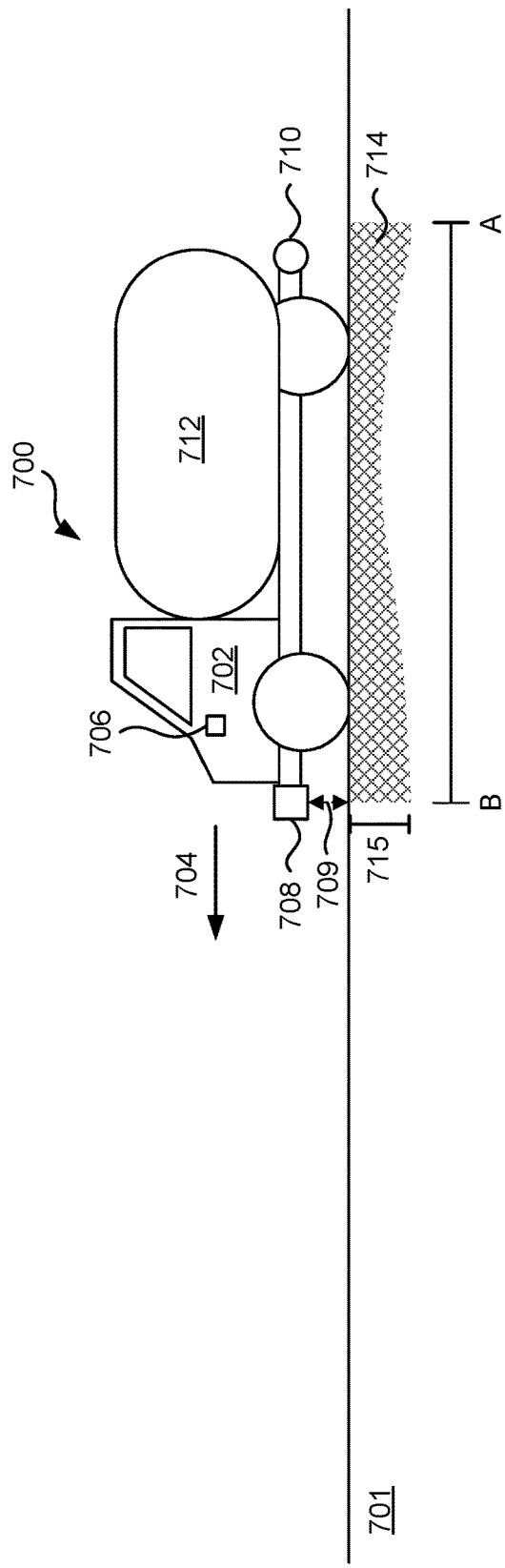
FIGS. 7A-7B are simplified illustrations of an exemplary dynamic soil moisture control system implemented in a water truck positioned at different locations along a path starting from a location at an open construction site, according to some embodiments of the present disclosure.
Figure 7B:
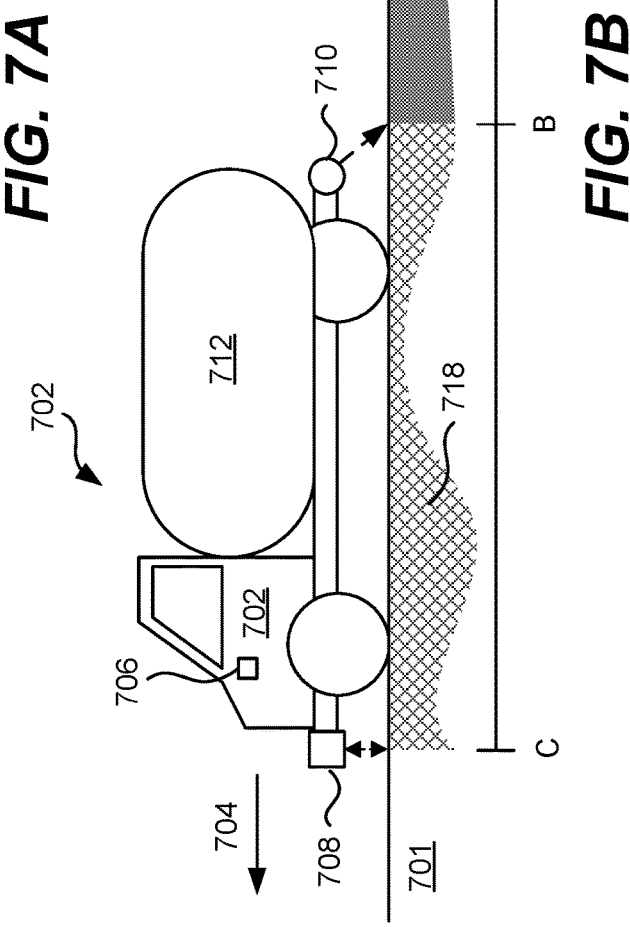

FIGS. 7A-7B are simplified illustrations of an exemplary dynamic soil moisture control system 700 implemented in a water truck 700 positioned at different locations along a path 704 starting from a location A at an open construction site, according to some embodiments of the present disclosure. Specifically, FIG. 7A is a simplified illustration of moisture control system 700 at a location B along path 704, and FIG. 7B is a simplified illustration of moisture control system 700 at a location C along path 704.

Dynamic soil moisture control system 700 can include a processor 706 coupled to a moisture sensor 708 and a water dispenser 710 for dispensing water from a water tank 712 onto soil 701 at the open construction site. Moisture sensor 708 can be positioned at the front of water truck 702 and be configured to measure a moisture level of soil 701 by sending and receiving signals 709 to and from various locations of soil 701. Water dispenser 710 can be positioned at the back of water truck 702 and be configured to dispense water through a series of nozzles (not shown). Water dispenser 710 can be an elongated structure of a certain width for dispensing water stored in water tank 712 across a wide area, as will be discussed herein with respect to FIGS. 9A-9B.

According to some embodiments of the present disclosure, dynamic soil moisture control system 700 can move along path 704 while measuring a current soil moisture content of soil 701 at a specific location, calculating a volume of water and application rate to dispense water at that location, and dispense the water on that location when water dispenser 710 is positioned accordingly. For instance, as shown in FIG. 7A, soil moisture control system 700 has traveled from location A to location B. During this movement from location A to B, moisture sensor 708 can continuously measure the current moisture content of soil 701 and store the measurement readings into memory. The measured moisture content can be associated with its location or time at which it was measured so that a moisture profile 714 across location A to B can be recorded, as shown in FIG. 7A.

As dynamic soil moisture control system 700 continues along path 704 to location C, dynamic soil moisture control system 700 can control water dispenser 710 to dispense the target volume of water over the respective locations measured by moisture sensor 708. As an example, when system 700 is at location B, moisture sensor 708 can measure a moisture level 715 of soil 701 and dispense a target volume of water at location B to raise the current moisture level 715 to the target moisture level when it is positioned to dispense water at location B, e.g., when system 100 is at location C as shown in FIG. 7B. This measuring and dispensing is performed on-the-fly such that dynamic soil moisture control system 700 is constantly dispensing and measuring as it moves along path 704 across the open construction site. Accordingly, as shown in FIG. 7B, as dynamic soil moisture control system 700 dispenses water at location B, it has already measured the moisture profile 718 of soil 701 between locations B and C and has already dispensed varying target volumes of water 716 between locations A and B according to moisture profile 714.

In some embodiments, moisture sensor 708 is configured to measure the moisture content across a line of soil. This allows dynamic soil moisture control system 700 to measure the current moisture level of a two-dimensional area of the open construction site as system 700 moves across the site. Thus, the dimensions of patches of soil at the open construction site that already have moisture, e.g., areas 210, 218, and 220 in FIG. 2, can be measured and taken into consideration by dynamic soil moisture control system 700 so that it can dispense the corresponding target volumes of water to avoid oversaturating those areas. In some embodiments, the width of the soil capable of being measured by moisture sensor 708 is equal to the width of the water dispensing capabilities of water dispenser 710. That way, there may be a one-to-one correlation between the location of soil measurements and the area of water dispensing. A better understanding of this concept can be ascertained by referencing FIGS. 8 and 9A-9B.

Figure 8:
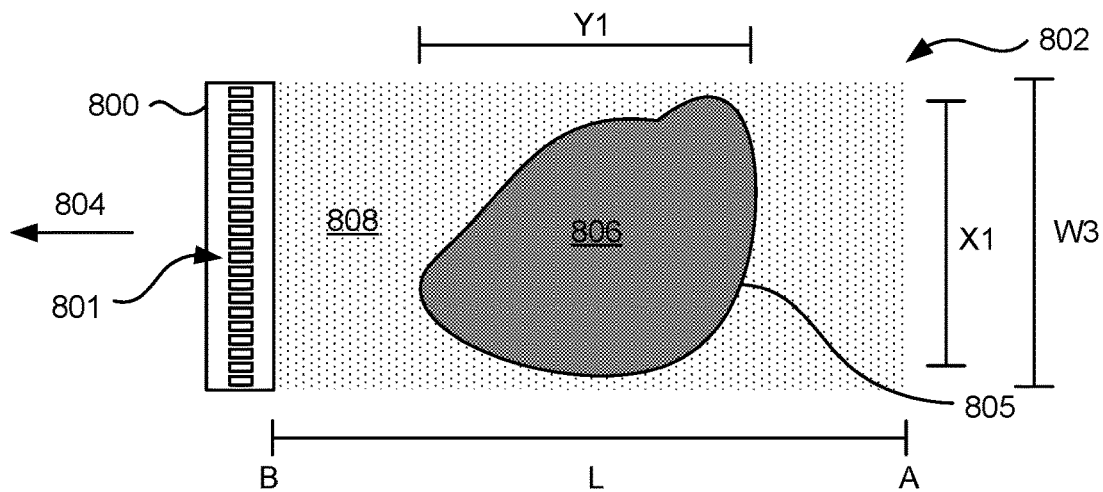
FIG. 8 is a diagram illustrating current moisture level measurements of soil between locations of an open construction site as measured by a moisture sensor, according to some embodiments of the present disclosure.
Figure 9A:
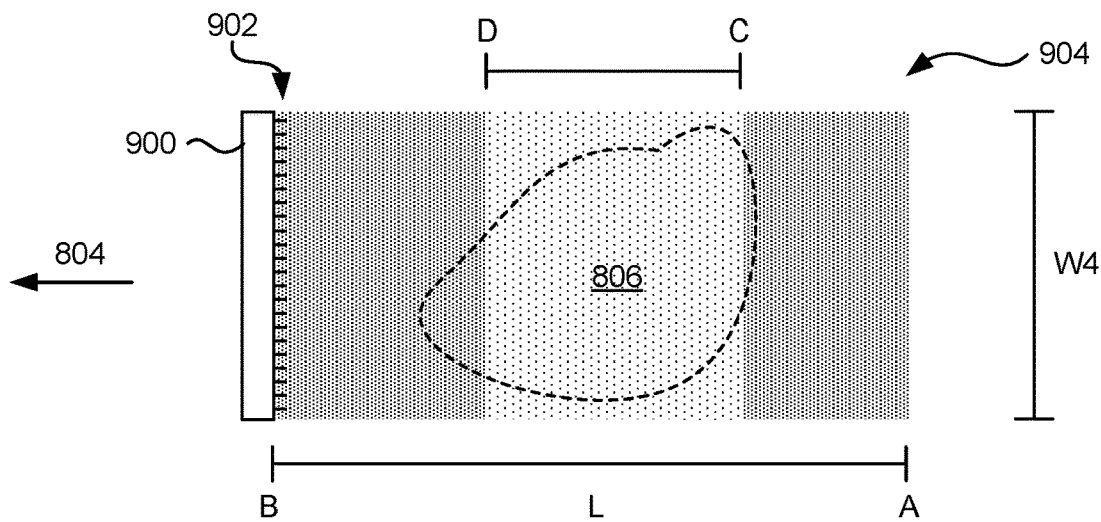
FIGS. 9A-9B are diagrams illustrating different volumes of water dispensed between locations of an open construction site by a water dispenser formed with a plurality of nozzles, according to some embodiments of the present disclosure.
Figure 9B:
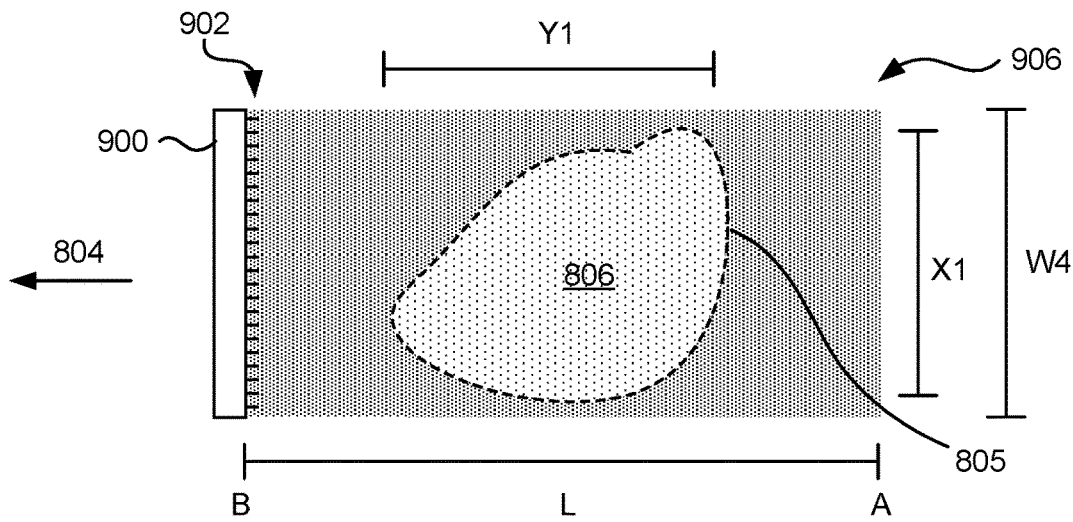

FIG. 8 is a diagram illustrating measurements of current moisture levels between locations A and B of an open construction site as measured by a moisture sensor 800, e.g., moisture sensor 708 in FIGS. 7A and 7B, according to some embodiments of the present disclosure; and FIGS. 9A-9B are diagrams illustrating different volumes of water dispensed between locations A and B of an open construction site by a water dispenser 900 formed with a plurality of nozzles 902, e.g., water dispenser 710 in FIGS. 7A and 7B, according to some embodiments of the present disclosure. The soil moisture control system can be configured to measure the current soil moisture level profile and dispense a volume of water at an application rate based on the current moisture level profile so that a more even distribution of moisture is achieved without substantially over-saturating or under-saturating certain regions of the soil.

For example, as shown in FIG. 8, moisture sensor 800 can measure a two-dimensional current moisture level profile 802 of the soil as the dynamic soil moisture control system moves along path 804. Current moisture level profile 802 can be defined by a width W3 and a length L, where width W3 is defined by the width of moisture sensor 800, and length L is defined by the distance traveled between locations A and B, which can be continually increasing as the system moves along path 804. As moisture sensor 800 continually scans the soil along path 804, the soil moisture control system can identify different moisture levels in the soil. For instance, moisture sensor 800 can identify that a region 806 of soil has a different amount of moisture than its surrounding area 808. Region 806 can have higher moisture than its surrounding area 808 when it is at a lower elevation where water can puddle. Or, region 806 can have lower moisture than its surrounding soil 808 when it is at a higher elevation where water can spread away. In some embodiments, moisture sensor 800 can be configured to measure a line of soil across width W3. For instance, moisture sensor 800 can be a plurality of sensors 801 arranged in a row as shown in FIG. 8, or it can be a single, elongated sensor (not shown).

The output of moisture sensor 800 can be a single value representative of the moisture level of the line of soil as a whole. In embodiments where the moisture sensor 800 is configured with plurality of sensors 801, the measurement value can be an aggregate of the measurements from plurality of sensors 801. This measurement value can be used by the soil moisture control system to dispense a pattern of water that complements current moisture level profile 802 measured by sensor 800. For instance, if the measurement value of the line of soil crosses a threshold moisture level, water dispenser 900 can dispense a different volume of water at a different application rate. As an example, if the measurement value is above a top threshold moisture level, which indicates that there is too much moisture currently in the soil, the soil moisture control system can decrease the volume of water and/or application rate, whereas if the measurement value is below a bottom threshold moisture level, which indicates that there is too little moisture currently in the soil, the soil moisture control system can increase the volume of water and/or application rate. The top and bottom threshold moisture levels can be above and below the target volume of water and application rate, respectively, so that if the moisture level is below the top threshold level and above the bottom threshold level, the water dispenser will continue to dispense the predetermined volume of water at the predetermined rate according to the calculations discussed herein with respect to FIGS. 5-6.

An example of this is shown in FIG. 9A. Water dispenser 900 can dispense water across a width W4 via nozzles 902. Width W4 can be substantially equal to width W3 so that the area of coverage by water dispenser 900 matches the area of measurement by moisture sensor 800. If it is determined that region 806 has a moisture level that is above the top threshold level, then the soil moisture control system can operate water dispenser 900 according to a water dispensing profile 904 that decreases the volume of water dispensed and/or application rate between locations C and D, i.e., where region 806 is located. Locations C and D can be points along path 804 where the measured moisture levels cross the top threshold level. For instance, location C can be the point where the measured moisture level increases past the top threshold level, and location D can be the point where the measured moisture level decreases past the bottom threshold level. Thus, water dispenser 900 can dispense a target amount of water at a target application rate from location A to location C, decrease the volume of water and/or application rate from location C to location D, and then increase the volume of water and/or application rate back to target levels from location D to location B. In some instances, locations C and D may not be positioned exactly where the edges of region 806 are positioned because the moisture levels may not cross the threshold value until a certain distance into region 806. By being able to dispense water according to the measured moisture level on-the-fly, the accuracy and uniformity at which the target amount of moisture is achieved across the open construction site by the water truck can be improved.

Although moisture sensor 800 in FIG. 8 can be configured to measure and output a single value that represents of the moisture level of the line of soil as a whole, embodiments are not so limited. Moisture sensor 800 can, in some additional or alternative embodiments, be configured to measure and output a set of multiple discrete values, each representing the moisture level at different discrete points along the line of soil. In such embodiments, the moisture control system can capture measurement values that correspond to the shape/profile 805 of region 806. For instance, the system can capture measurement values that correspond to the two-dimensional shape of region 806 having a width X1 and a length Y1 with various profile contours as shown in FIG. 8. With this information, the soil moisture control system can control water dispenser 900 to dispense a pattern of water that complements the two-dimensional profile of region 806.

An example of this is shown in FIG. 9B. Water dispenser 900 can dispense water according to a water dispensing profile 906 that substantially matches the measured moisture level profile 802 of the soil (see FIG. 8). That is, the outer profile of the water dispensed in region 806 can substantially conform to the measured shape/profile 805 of region 806 as shown in FIG. 9B. Accordingly, the volume of water and/or application rate of water dispensed within region 806 can have a width X1 and a length Y1 with various profile contours that match profile 805 of region 806 as shown in FIG. 9B. By being able to dispense water with such flexibility, the accuracy and uniformity at which the target amount of moisture is achieved across the open construction site by the water truck can be substantially improved.

In some embodiments, water dispenser 900 can be configured so that all the nozzles output the same volume of water and at the same application rate. That way, the entire line of soil can be watered at the same time, which enables the functionality discussed herein with respect to FIG. 9A. In such embodiments, water dispenser 900 can have a single valve that controls the flow of water through each nozzle. In some additional or alternative embodiments, water dispenser 900 can be configured so that each nozzle is independently controllable so that some nozzles can output different volumes of water and at different application rates than other nozzles. That way, discrete sections of the line of soil can be watered at a time, which enables the functionality discussed herein with respect to FIG. 9B. In such embodiments, water dispenser 900 can have a separate valve for each nozzle, or subset of nozzles, so that some valves can be turned on to dispense water on soil that needs more moisture while some other valves can be turned off to not dispense water on soil that has already achieved a desired level of moisture, or scaled back to dispense less water on soil that is almost at the target moisture level.

V. Method of Dynamic Autonomous Soil Moisture Control

Figure 10:
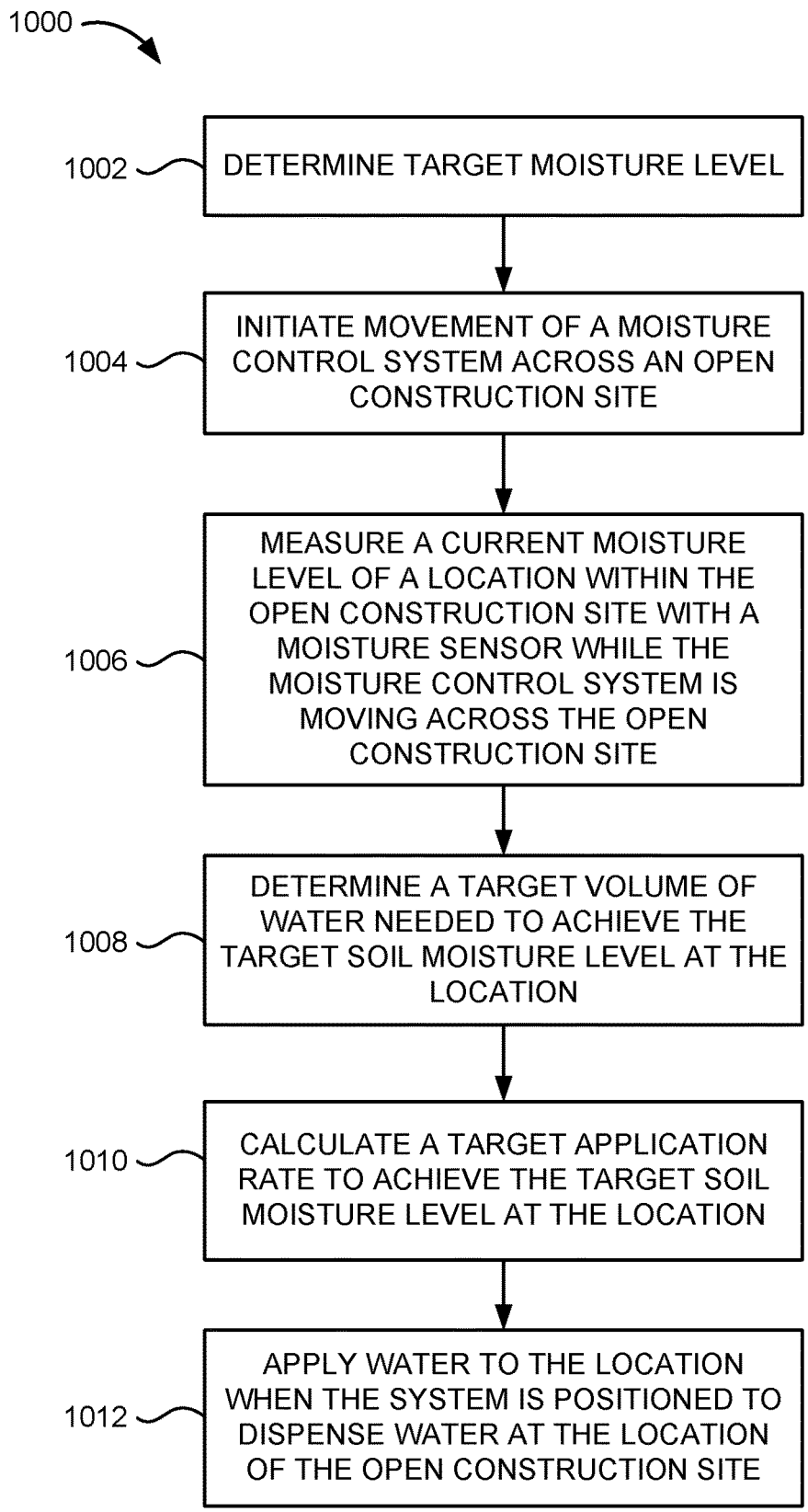
FIG. 10 is a flow chart of an exemplary method of dynamic autonomous soil moisture control performed by a soil moisture control system for achieving uniform and suitable levels of moisture across an open construction site, according to some embodiments of the present disclosure.

FIG. 10 is a flow chart 1000 of an exemplary method of dynamic autonomous soil moisture control performed by a soil moisture control system for achieving uniform and desired levels of moisture across an open construction site, according to some embodiments of the present disclosure.

At block 1002, a target moisture level can be acquired. For instance, the target soil moisture level can be calculated by an engineer or scientist surveying the soil moisture at the open construction site and then determined by the soil moisture control system via user input through an input device. Alternatively, the target soil moisture level can be determined based on the specific goal to be achieved. For dust control, the target soil moisture level may be an amount of moisture that minimizes dust from being ejected into the atmosphere when construction activity is performed on the open construction site. In such instances, the target soil moisture level can be any level of moisture greater than a moisture level threshold without an upper moisture limit as there may not be a great concern for soil oversaturation for dust control. For soil compaction, the target soil moisture level may be an amount of moisture that achieves a target compaction level. In such instances, the target soil moisture level can be a range of moisture levels between a minimum moisture level and a maximum moisture level. The target soil moisture level can also depend on soil type. Different soil types can have different binding characteristics and thus require different moisture levels to enable sufficient soil compaction. A single open construction site can include many different soil types. Thus, an open construction site can have different target soil moisture levels for different areas of the open construction site.

Then, at block 1004, movement of the soil moisture control system across the open construction site can be initiated. For instance, the soil moisture control system can output a graphical interface to a user to initiate movement of the water truck. The graphical interface can be displayed to the user on a display that indicates to the user to move the water truck. In additional or alternative embodiments, the soil moisture control system can autonomously instruct a vehicle control module to initiate movement of the water truck. In such embodiments, the system can autonomously initiate movement of the water truck without involvement of a user. In some embodiments, a planned path across the open construction site to achieve a desired level of uniformity of moisture across the open construction site may first be determined by the soil moisture control system before initiating movement of the system. For instance, a predetermined path, e.g., path 306 discussed herein with respect to FIG. 3, can be calculated by the dynamic soil moisture control system based on the dimensions of the open construction site and a width of water coverage dispensed by the water truck. The predetermined path can be determined so that edges of water coverage are positioned to mitigate or completely eliminate gaps and overlaps in water coverage to ensure that the entire surface area of the open construction site receives a correct amount of moisture.

At block 1006, a current moisture level of a first location within the open construction site is measured with a moisture sensor while the soil moisture control system is moving across the open construction site. For instance, a moisture sensor mounted at the front of the water truck can measure the current moisture level of the soil at a location, e.g. a line of soil at location B in FIG. 7A, as it moves across the open construction site, as discussed herein with respect to FIGS. 7A-7B.

Then, at block 1008, a target volume of water needed to achieve a target soil moisture level can be determined. In some embodiments, the target volume of water can be determined based on the measured current soil moisture level at the location and the target soil moisture level at the location. The target volume of water can be a volume of water that achieves the target soil moisture level when dispensed into the soil at the location in the open construction site.

The soil moisture control system can then, at block 1010, use the determined target volume of water to calculate a target application rate to dispense on the soil at the location in the open construction site to achieve the target soil moisture level. The target application rate can be based on several factors, such as flow rate limits of the nozzles that dispense the water, capacity of the tank storing the water, the speed at which the truck is moving across the open construction site while it is dispensing water, and other factors, as discussed herein with respect to block 410 in FIG. 4.

Then, at block 1012, when the system is positioned to dispense water at the location, the water dispenser can apply the determined target volume of water at the target application rate to the location in the open construction site. In some embodiments, the soil moisture control system can instruct the water dispenser to apply the target volume of water at the target application rate evenly across the line of soil, as discussed herein with respect to FIG. 9A, or to apply the target volume of water at the target application rate differently across different discrete locations along the line of soil, as discussed herein with respect to FIG. 9B to achieve an accurate and even distribution of moisture across the open construction site. In some embodiments, the water dispenser can apply the determined target volume of water at the location while the moisture sensor is concurrently measuring the current moisture level of a different location in the open construction site along the path of travel. Accordingly, the dynamic soil moisture control system can enable the water truck to measure and dispense water at the open construction site on-the-fly.

According to some embodiments, the dynamic soil moisture control system can determine that it is positioned to dispense water over the location using various methods. For instance, a GPS device can be located on the moisture sensor so that the measurements can be associated with a specific location in the open construction site. And, a GPS device can be located on the water dispenser so that the dynamic soil moisture control system can determine that the water dispenser is suitably positioned to dispense water at the location at which the moisture level was measured. Additionally or alternatively, the dynamic soil moisture control system can calculate the specific instance when the water dispenser is suitably positioned to dispense water at the specific location. For instance, the dynamic soil moisture control system can use its current speed and known distance between the moisture sensor and the water dispenser to calculate when the water dispenser will be positioned to dispense water at the location. If the speed of the system changes, e.g., slows down or speeds up due to surface topography and/or obstacles, the calculation can be adjusted accordingly. For instance, if the system slows down, then the system can calculate that the water dispenser will be suitably positioned to dispense water at the location at a later time. It is to be appreciated that any other suitable method can be used to determine when the water dispenser is suitable positioned without departing from the spirit and scope of the present disclosure.

In some embodiments, the water dispenser can be dispensing water as the dynamic soil moisture control system is guiding the water truck over a path across the open construction site. The path can be determined by the dynamic soil moisture control system. In some embodiments, the dynamic soil moisture control system can output a graphical interface to a user to guide the user along the path at a predetermined speed. The graphical interface can be displayed to the user on a display that indicates to the user where to drive water truck along the open construction site and what speed. In additional or alternative embodiments, the dynamic soil moisture control system can autonomously instruct a vehicle control module to steer the water truck at the predetermined speed without user involvement.

By being configured to perform method 1000, dynamic soil moisture control systems, according to some embodiments of the present disclosure, can very accurately and uniformly dispense an amount of moisture across an open construction site to achieve a target moisture level with little to no user involvement. Such systems can thus result in a water truck that is improved over conventional water trucks.

VI. Autonomous Soil Moisture Control System

Figure 11:
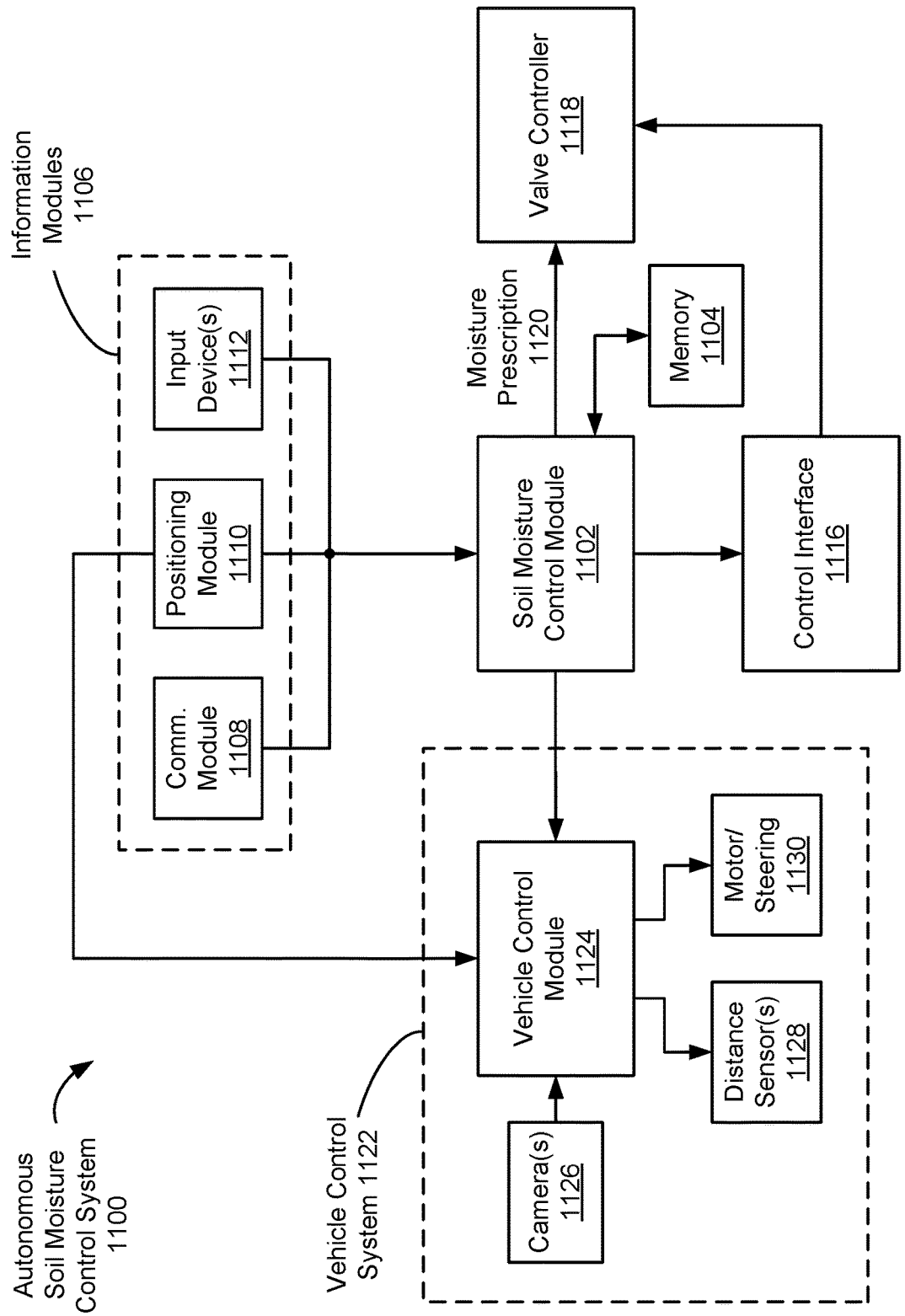
FIG. 11 is a block diagram of an exemplary autonomous soil moisture control system, according to some embodiments of the present disclosure.

FIG. 11 is a block diagram of an exemplary autonomous soil moisture control system 1100, according to some embodiments of the present disclosure. System 1100 can be implemented in a water truck to improve its operation by performing any of the methods discussed herein to achieve an accurate and uniform amount of moisture across an open construction site. Soil moisture control system 1100 can include a soil moisture control module 1102 that can be formed of one or more processors. Soil moisture control module 1102 can receive a series of inputs, perform computations based on those inputs, and send outputs to various other components to instruct them on their operation, as aforementioned herein. Soil moisture control module 1102 can be coupled to memory 1104 in which lines of code for instructing the operation of soil moisture control module 1102 can be stored. Additionally, memory 1104 can store data that is used by soil moisture control module 1102 to perform its computations. For instance, site characteristics 1114 including current moisture levels, current site characteristics, future site characteristics, predictive models, evaporation rates, and the like, can be stored in memory 1104.

Autonomous soil moisture control system 1100 can also include one or more information modules 1106 that can be coupled to soil moisture control module 1102 so that input data generated by the sources 1106 can be provided to soil moisture control module 1102. As an example, information modules 1106 can include at least a communication module 1108, positioning module 1110, and one or more input devices 1112.

Communication module 1108 facilitates communication with other devices over wireless circuitry through a wireless network (e.g., the Internet, wireless LAN, LTE, GSM, etc.) and includes various software components for handling data received from the wireless circuitry. By being coupled to communication module 1108, soil moisture control module 1102 can determine current and/or future site characteristics of an open construction site, as discussed herein with respect to FIG. 4. Soil moisture control module 1102 can also be remotely controlled to autonomously control the soil at the open construction site.

Positioning module 1110 can be any suitable positioning system, such as a global positioning system (GPS) or any other global or local triangulation system for determining the position of the autonomous soil moisture control system 1100. By being coupled to positioning module 1110, soil moisture control module 1102 can determine its location within the open construction site so that it can traverse along a predetermined path, e.g., path 306 or path 704 discussed herein with respect to FIGS. 3 and 7.

One or more input devices 1112 can be any suitable input device such as a button, keyboard, touch screen, sensors, and the like. As an example, one or more input devices 1112 can be a moisture sensor, e.g., moisture sensor 708 or moisture sensor 800 discussed herein with respect to FIGS. 7A-7B and 8.

In some embodiments, soil moisture control module 1102 can receive data from information sources 1106 and use this data to determine current and/or future site characteristics of an open construction site, calculate forecast evaporation rates, determine a predictive model of future site characteristics of the open construction site, determine a target volume of water needed to achieve a target soil moisture level, calculate a target water application rate to achieve the target soil moisture level, and determine a planned path across the open construction site, as discussed herein with respect to FIG. 4

Autonomous soil moisture control system 1100 can also include a control interface 1116 and a valve controller 1118 coupled to soil moisture control module 1102. Control interface 1116 can be any suitable user interface, such as a display screen, touch screen, keyboard, and the like for outputting information to a user, e.g., a driver of the water truck, and/or receiving input information. In some embodiments, control interface 1116 can include an input device from one or more input devices 1112. Valve controller 1118 can be included in a water dispenser that controls the operation of one or more valves to dispense water onto the soil through one or more nozzles, as discussed herein with respect to FIGS. 9A and 9B. By being coupled to control interface 1116 and 1118, soil moisture control module 1102 can send instructions to control interface 1116 to guide system 1100 along the predetermined path and send a moisture prescription 1120 to valve controller 1118 to dispense water at the target application rate to achieve the target moisture level, as discussed herein with respect to FIG. 4. Moisture prescription 1120 can include instructions or commands for directing valve controller 1118 to dispense the correct volume of water at the correct application rate. Guidance of system 1100 can be performed by instructing a driver of the water truck via the control interface 1116. In some embodiments, control interface 1116 can be coupled to valve controller 1118 so that the user can control the dispensing of water, such as to cease operation in an emergency event.

As discussed herein, soil moisture control system 1100 can, in some embodiments, guide the water truck autonomously, i.e., without user involvement. Thus, autonomous soil moisture control system 1100 can be configured to interact with a vehicle control system 1122. In some embodiments, vehicle control system 1122 can be implemented in a water truck and can include a vehicle control module 1124 that is coupled to one or more cameras 1126, one or more distance sensors 1128, and motor/steering 1130. Vehicle control module can be configured to receive information from camera(s) 1126 and distance sensor(s) 1128, which can be any suitable ranging device such as LIDAR, to safely and appropriately drive the water truck along the predetermined path by controlling motor/steering 1130 without user involvement. In such embodiments, vehicle control module 1124 can be coupled to positioning system 1110 so that vehicle control module can know the positioning of system 1100 in relation to the open construction site. Furthermore, communication module 1108, in such embodiments, can be configured to send data through the wireless network to inform a user located in a location separate from system 1100 about the water dispensing status of autonomous soil moisture control system 1100. Communication module 1108 can also receive instructions from a user that is at a location separate from system 1100 to remotely control the operation of system 1100. By guiding water truck along the predetermined path while dispensing the target volume of water at the target application rate, autonomous soil moisture control system 1100 can very accurately and uniformly dispense an amount of moisture across an open construction site to achieve a target moisture level with little to no user involvement.

Although the invention has been described with respect to specific embodiments, it will be appreciated that the invention is intended to cover all modifications and equivalents within the scope of the following claims.

What is claimed is:

1. A method for moisturizing soil at an open construction site, comprising:
   determining a target degree of compaction for the soil at the open construction site;
   determining, by a soil moisture control system, a target soil moisture level for achieving the target degree of compaction of the soil at the open construction site;
   measuring, by the soil moisture control system, a current soil moisture level of a location within the open construction site with a plurality of moisture sensors arranged perpendicular to a direction of travel while the soil moisture control system is moving along a predetermined path across the open construction site;
   storing, by the soil moisture control system, the current soil moisture level of the location in memory;
   determining, by the soil moisture control system, a target volume of water for achieving the target soil moisture level at the location based on the current soil moisture level at the location;

calculating, by the soil moisture control system, a target application rate to achieve the target soil moisture level at the location based on the target volume of water; and applying, by the soil moisture control system, the target volume of water at the target application rate to the location when the soil moisture control system is positioned to dispense water at the location of the open construction site.

2. The method of claim 1, wherein the location is a first location and the method further comprises measuring, by the soil moisture control system, a current moisture level of a second location within the open construction site with the plurality of moisture sensors while the soil moisture control system is moving along the predetermined path across the open construction site.

3. The method of claim 2, wherein the second location is located at a point farther along the predetermined path than the first location.

4. The method of claim 2, wherein the measuring of the current moisture level of the second location occurs while the soil moisture control system is dispensing water at the first location.

5. The method of claim 1, wherein the target soil moisture level is based on binding characteristics of the soil to minimize dust or to achieve a certain level of soil compaction.

6. The method of claim 1, wherein determining the target volume of water is based on a difference between the target soil moisture level and the current soil moisture level.

7. The method of claim 1, wherein determining the target volume of water is based on forecast evaporation rates of the open construction site and a time at which a construction activity is to be performed at the open construction site following dispensing of water at the open construction site.

8. The method of claim 1, wherein the location is a line of soil measureable by the plurality of moisture sensors.

9. The method of claim 8, wherein the soil moisture control system includes a water dispenser configured to dispense different volumes of water at different locations along the line of soil.

10. The method of claim 9, wherein the water dispenser includes a plurality of independently controllable nozzles.

11. A computer product comprising a non-transitory computer readable medium storing a plurality of instructions that when executed control an electronic device including one or more processors, the instructions comprising:

accessing a target degree of compaction for soil at an open construction site;

determining, by a soil moisture control system, a target soil moisture level for achieving the target degree of compaction of the soil at the open construction site;

measuring, by the soil moisture control system, a current soil moisture level of a location within the open construction site with a plurality of moisture sensors arranged perpendicular to a direction of travel while the soil moisture control system is moving along a predetermined path across the open construction site;

storing, by the soil moisture control system, the current soil moisture level of the location in memory;

determining, by the soil moisture control system, a target volume of water for achieving the target soil moisture level at the location based on the current soil moisture level at the location;

calculating, by the soil moisture control system, a target application rate to achieve the target soil moisture level at the location based on the target volume of water; and applying, by the soil moisture control system, the target volume of water at the target application rate to the location when the soil moisture control system is positioned to dispense water at the location of the open construction site.

12. The computer product of claim 11, wherein the location is a first location and the instructions further comprise measuring, by the soil moisture control system, a current moisture level of a second location within the open construction site with the plurality of moisture sensors while the soil moisture control system is moving along the predetermined path across the open construction site.

13. The computer product of claim 12, wherein the second location is located at a point farther along the predetermined path than the first location.

14. The computer product of claim 12, wherein the measuring of the current moisture level of the second location occurs while the soil moisture control system is dispensing water at the first location.

15. The computer product of claim 11, wherein the target soil moisture level is based on binding characteristics of the soil to minimize dust or to achieve a certain level of soil compaction.

16. A system for moisturizing soil at an open construction site, comprising:

one or more information modules configured to receive and send information, the one or more information modules including a plurality of moisture sensors positioned at a front of a water truck and arranged perpendicular to a direction of travel;

memory configured to store data;

a water dispenser positioned at a back of the water truck and configured to dispense water through one or more nozzles into the soil at the open construction site;

a control interface for displaying information to a user; and a soil moisture control module formed of one or more processors coupled to the one or more information modules, the memory, the water dispenser, and the control interface, wherein the soil moisture control module is configured to:

determine a target soil moisture level for the soil at the open construction site;

measure a current soil moisture level of a first location on a line of soil and a current soil moisture level of a second location on the line of soil within the open construction site with the plurality of moisture sensors while the system is moving along a predetermined path across the open construction site, wherein the line of soil is perpendicular to the predetermined path;

store the current soil moisture level of the first and second locations in memory;

determine a first target volume of water for achieving the target soil moisture level at the first location based on the current soil moisture level at the first location;

determine a second target volume of water for achieving the target soil moisture level at the second location based on the current soil moisture level at the second location;

calculate a first target application rate and a second target application rate to achieve the target soil moisture level at the first and second locations based on the first and second target volumes of water; and apply the first and second target volumes of water at the first and second target application rates to the first and second locations respectively when the system is positioned to dispense water at the first and second locations of the open construction site.

17. The system of claim 16, wherein the one or more information modules include at least one of a communication module, a positioning module, and an input device.

18. The system of claim 16, wherein the soil moisture control module is coupled to a vehicle control system that includes a vehicle control module for controlling an operation of the water truck without user involvement.

19. The system of claim 18, wherein the vehicle control system further includes a camera, a distance sensor, and a motor with steering to control the operation of the water truck.

20. The system of claim 16, wherein the soil moisture control module is further configured to determine current site characteristics of the open construction site, the current site characteristics including at least one of a temperature at the open construction site, wind speed and direction at the open construction site, and a slope gradient of one or more areas of the open construction site.

* * * * *